United States Patent [19]

Drummond

[11] 4,409,968

[45] Oct. 18, 1983

[54] METHOD AND APPARATUS FOR ENGAGING A HOOK ASSEMBLY TO A SPINAL COLUMN

[76] Inventor: Denis S. Drummond, 1214 Wellesley St., Madison, Wis. 53703

[21] Appl. No.: 255,249

[22] Filed: Apr. 17, 1981

Related U.S. Application Data

[62] Division of Ser. No. 118,315, Feb. 4, 1980, abandoned.

[51] Int. Cl.³ .............................................. A61F 5/00
[52] U.S. Cl. .................................................... 128/69
[58] Field of Search .................... 128/69, 92 R, 92 A, 128/84 B, 87 R, 1 R

[56] References Cited

U.S. PATENT DOCUMENTS

| | | | |
|---|---|---|---|
| 4,041,939 | 8/1977 | Hall | 128/69 |
| 4,078,559 | 3/1978 | Nissinen | 128/69 |
| 4,269,178 | 5/1981 | Keene | 128/69 |

OTHER PUBLICATIONS

"Spine Instrumentation-Harrington", *Zimmer Catalog*, 1973, (Feb.), pp. D67–D72.

*Primary Examiner*—Richard J. Apley
*Assistant Examiner*—T. J. Wallen
*Attorney, Agent, or Firm*—Sherman & Shalloway

[57] ABSTRACT

A method and apparatus for use in the treatment of spinal fractures and scoliosis. Windowed hook holders are used to firmly grasp and position hooks having a slotted base and a projecting hook on the spinal column. The projecting hook is used to engage the bone of the spinal column.

Two or more hooks are held firmly in place on the spinal column with the hook holders. A threaded rod carrying two or more sleeves which are slideable along the length of the rod and locking nuts are aligned with the hooks and the sleeves and nuts spaced along the rod to correspond approximately to the spacing of the positioned hooks.

The threaded rod, sleeves and nuts are then passed through the window openings of the hook holders and aligned with the hooks without disengaging the hook holders from the hooks. The threaded rod is then dropped into the slots and the sleeve slid into the hook base to hold the rod in the hook. Opposing openings are located on either side of the base for engagement by the hook holder, to aid in the placement of the hook and to hold the hook before and during interconnection with the threaded rod. Preferably, the hook assembly forms a part of a Harrington compression rod or a tensioning means which interconnects a Harrington distraction rod and a Harrington compression rod. Adjustment of the locking nut locks the hook to the rod.

8 Claims, 14 Drawing Figures

METHOD AND APPARATUS FOR ENGAGING A HOOK ASSEMBLY TO A SPINAL COLUMN

This is a division, of copending application Ser. No. 118,315, filed Feb. 4, 1980 abandoned.

BACKGROUND OF THE INVENTION

1. Field of the Invention

The invention relates to a method and apparatus for use in the surgical treatment of spinal fractures or for straightening the spine in the surgical treatment for deviations of the spinal column, especially scoliosis. The present invention particularly relates to an apparatus for installing a hook assembly for a Harrington spinal rod which is affixed to the spine. More particularly, the invention relates to a novel hook holder for holding the hooks in position while they are assembled on a compression rod.

2. Description of the Prior Art

Scoliosis is the lateral deviation of the spinal column. The spinal curvature which results from scoliosis is generally defined on the basis of specific reference points. In particular, the extreme upper and lower vertebrae and the most displaced vertebra are of particular interest. The extreme upper and lower vertebrae are those which are the most inclined relative to the median longitudinal axis of the torso. The two planes within which the extreme upper and lower vertebrae can be found define the scoliotic angle. The most displaced vertebra is defined as the vertebra which is the farthest from the median axis of the torso.

When the scoliotic angle of curvature exceeds a given limit of approximately 35°–50°, it becomes necessary to consider surgical treatment of the scoliosis. The surgical treatment is known as arthrodesis and consists of fusing together the vertebrae of the scoliotic curvature, after correcting the scoliotic curvature to the maximum possible extent. Such correction can be accomplished prior to the operation by continuous traction of the spine or by corrective plaster casts.

However, it is during surgery that the correction is completed and finalized. For this purpose, a solid metallic rod with hooks is placed in the concavity of the curvature and a threaded rod with hooks is placed on the convexity of the curvature. These rods straighten the spine and maintain the correction until arthrodesis is attained by means of autogenous bone graft. The prior art implants used most often to correct curvature during surgery are known as the Harrington distraction system and the Harrington compression system, illustrated in FIG. 1.

The distraction system consists of two metallic anchoring devices 116 and 117 of the hook type which are attached to the vertebrae 4 which comprise the spinal column, generally referred to by reference character 1. A notched metal rod 115 serves as a stay and permits the spacing between the hooks 116 and 117. One of the ends 118 of rod 115 is usually notched in such a manner as to permit the distance between anchoring devices 116 and 117 to be adjusted by means of a spreading instrument. Generally, the upper anchoring element 116 is intended for fastening toward the upper end of the spine and is hooked onto a dorsal vertebra 9. Usually the hook of element 116 is directed upward and shaped in such a manner as to permit its insertion between the articular facets of two adjacent vertebrae. The hook of element 116 penetrates into the interarticular space and is supported on the vertebra.

Similarly, a lower anchoring element 117 is intended to be fastened at the lower end of the spine and is often supported on a lumbar vertebra 10. It is contemplated that the hook associated with element 117 is directed downwardly and supported on the lamina of the lumbar vertebra between the spinous process and the articular facet. In the illustrated example, vertebrae 9 and 10 are considered to be the extreme vertebrae.

The compression system consists of two or more metallic anchoring devices 111 and 112 of the hook type which are attached to selected transverse processes of vertebrae 4 which are situated on the convex side of the scoliotic curvature. Threaded metal rod 113 serves as a stay and permits spacing between the hooks 111 and 112. Hooks 111 and 112 usually face each other and slide freely along threaded rod 113. These hooks are adjusted by means of nuts 114 so as to effect compression of the convexity of the scoliotic curvature. It is understood that more than two hooks and nuts can be used to achieve the desired amount of compression.

Thus, by the application of Harrington distraction and compression systems, the straightening of the scoliotic curvature can be effected and maintained. Vertebral arthrodesis is then achieved by exposing the posterior arches of the vertebrae and attaching autogenous spongy bone with the Harrington devices left in place.

FIG. 2 is an illustration of a patient suffering from scoliosis schematically represented from the back. The spinal column 1 is visible and indicated schematically by rectangles or trapezoids. The patient illustrated in FIG. 2 exhibits a scoliosis involving a deviation of the vertebrae to the right. The scoliotic curvature can be defined on the basis of the top vertebra 2 and the bottom vertebra 3 of the deviation, and the vertebrae 4 which are located at the peak of the curvature. It is noted that the vertebrae 2 and 3 are those which are most strongly inclined relative to the median longitudinal axis M-M of the body, while vertebrae 4 are those which are farthest from that axis. Angle $\alpha$ is thus a characteristic of the scoliotic curvature. When the angle $\alpha$ exceeds a limit of approximately 35°–50°, it is often necessary to resort to arthrodesis and to install Harrington distraction and compression rod systems, as illustrated in FIG. 1.

However, the Harrington distraction and compression systems are not totally effective in supporting the peak vertebrae 4 which are further away from the axis M-M than the other vertebrae and cannot fully accomplish straightening of the scoliotic curvature. Accordingly, transverse tensioning devices as illustrated in FIGS. 3 and 4 have been suggested by French Pat. No. 2,244,446. Such a transvere tensioning device makes use of (1) a compression rod 11, similar to the Harrington compression rod, and (2) a tensioning element 12. Obviously, the intent of the Harrington distraction rod 5 is to separate the vertebrae apart from each other. The basis of the transverse tensioning device is a tensioning element 12 which is supported by the compression rod 11 on the side of the vertebrae most displaced by the curvature and connected to the other side of the spine by the Harrington distraction rod 5. Preferably, the tensioning means is adjustable so that the peak of the scoliotic curvature can be pulled toward the distraction rod 5, resulting in a better correction of the curvature and a better preservation of the correction obtained. It is contemplated that a transverse tensioning device results in reduction of the lateral displacement of the most displaced vertebrae, completion of the correction obtained by the longitudinal Harrington distraction rod, and relief of the load on the supporting vertebrae.

Generally, the transverse tensioning devices of the prior art have been comprised of compression rod 11 and tensioning element 12, the first of which is intended to be supported on two vertebrae 4 which are closest to the peak of the scoliotic curvature and the second of which permits the first to be brought nearer to the metallic distraction rod 5.

Compression rod 11 is generally comprised of a threaded rod 13, at one end of which is permanently fastened a hook 14. This rod 13 passes freely through another hook 15 which is held in place by nuts 16. Hook 15 slides along rod 13 and faces hook 14. Hook 14 has a rounded and beveled end 17 which allows it to be supported, from top to bottom, by the transverse processes of the upper vertebrae 4 of the peak, after cutting of the costotransverse ligament. Hook 15 passes from the bottom to top beneath the transverse process of the lower vertebrae 4 of the peak. Nut and locking nut 16 permit hooks 14 and 15 to be brought closer to each other and to be tightened in such a way as to effect a firm transverse grip. Hook 15 is finally locked into position by means of a set screw S which jams the threads of rod 11. Hooks 14 and 15 are attached to the transverse processes of vertebra 4 which are situated on the convex side of the scoliotic curvature.

Tensioning element 12 comprises a threaded rod having one end which is permanently fastened to hook 18. The rod passes freely through another hook 19 which is held in place on the rod by nuts 20 and 21. Hook 19 is able to slide along the rod and faces hook 18. Hook 18 engages rod 13 and hook 19 engages Harrington rod 5. By screwing nut 21 and locking nut 20 along the rod hooks 18 and 19 approach each other and the peak vertebrae 4 are made to approach median axis M-M. This allows better correction of the scoliotic curvature. Hook 19 is finally locked into position by means of set screws which jam the threads of element 12. It is noted that elements 11 and 12 are located at the posterior side of the spine, element 12 being in contact with the spongy graft 41 necessary for this arthrodesis so as to reinforce the solidity of the arthrodesis.

The surgical techniques used in employing the transverse traction device illustrated in FIGS. 3 and 4 are outlined in more detail by Dr. Cotrel in his article entitled "New Techniques for the Treatment of Idiopathic Scoliosis", *International Orthopedics,* Spring, 1978, pp. 247-265.

The difficulty with using the Harrington system is that it requires attaching of all of the hooks on the compression rod or traction device prior to attaching the hooks to the spinal column. With the Harrington system, all of the compression hooks must be premounted on the compression rod prior to their simultaneous seating on the transverse processes of the vertebra to be instrumented.

Frequently, the hooks unseat while an adjacent level is being instrumented. It is also difficult to keep all the hooks in place before adding compression, particularly if the deformity of the spine is an extensive one. If one hook is displaced during instrumentation, it is often impossible to reset it without removing all the hooks and starting over.

The use of the recently developed slotted hook system has to a large extent overcome many of the problems inherent in the Harrington system.

The slotted hook system, however, until applicant's development of the windowed hook holder, still had some significant draw backs.

The major problem encountered when using slotted hooks was that they had to be held securely in place while the spinal rod was inserted in the slots. Heretofore, when installing slotted hooks, it had been necessary to disengage the hook holder from the hook to allow the compression rod to fit through the slot in the hook. Then the hook holder had to be repositioned on the hook to seat the rod in the hook. This required disengaging of the prior art hook holder as each hook was located on the spinal rod. This procedure severely hampered the surgeon's control over the individual hooks when inserting the compression rod into each hook. Since as many as six or eight hooks are sometimes inserted in one patient, the prior art procedure made insertion of the compression rod in the hooks relatively difficult and time consuming.

SUMMARY OF THE INVENTION

It is an object of this invention to provide a hook holder for use with a slotted hook and system for use with a threaded Harrington compression rod which may be used for the treatment of scoliosis or spinal fractures, the hook holder and hook assembly allowing a surgeon to easily place the Harrington rod in position.

It is a further object of this invention to provide a hook holder and hook assembly for a threaded Harrington compression rod which allows the hooks to be easily and properly spaced on the Harrington rod.

It is a further object of this invention to provide a hook holder and hook assembly for a Harrington compression rod which allows the hooks to be tilted and manipulated into position before engaging the rod and being retained on the rod.

It is a further object of this invention to provide a hook holder having an open area behind the jaws of the holder which forms a window opening in the jaw portion of the hook holder.

It is another object of this invention to describe a hook assembly for use in combination with a Harrington compression rod which reduces the amount of laminectomy when hooks are being placed on the laminae.

It is a further object of this invention to provide a hook assembly for use with a Harrington compression rod which has a radiused shoe on each hook which can be placed to clear the edge of the lamina before the rod is tightened to achieve compression or distraction.

It is a further object of this invention to provide a hook holder for holding a slotted hook and placing the hook in position on the spine and holding the hook in position while dropping and inserting a Harrington compression rod into the slot on the hook without releasing the hook from the hook holder.

It is a further object of this invention to provide a hook holder having an open area immediately behind the jaws of the holder which allows passing a Harrington compression rod through the open area behind the jaws, while the jaws hold a slotted hook, and dropping and inserting a Harrington compression rod into the slot on the hook without releasing the hook from the hook holder.

It is another object of this invention to provide a hook holder for use with slotted hooks and a threaded Harrington rod which includes a slotted hook comprised of a base and projecting hook, the base having a bore therethrough for receiving a sleeve located on the rod.

It is yet another object of this invention to provide a hook holder and hook assembly for positioning and holding a Harrington compression rod which allows the preliminary placement of the hook and rod without release of the hook from the hook holder before and while engaging the rod.

It is a final object of the hook assembly of this invention to provide a system for use in combination with a Harrington compression rod which significantly reduces the surgical time required for installing such rods.

The present invention relates to a windowed hook holder and slotted hook and to the use of the hook holder to install the slotted hook and spinal rod for engaging the spine.

The present invention provides a method of using a windowed hook holder which allows individual holding of slotted hooks, manipulation and adjustment of the hooks and passage of a spinal rod through the windowed opening in the hook holder and placement of the spinal rod in the slot of the hooks without having to disengage the hook holder from the hook.

The slotted hooks can be independently seated and firmly held in position on the spine by the hook holders while the threaded spinal rod with the sleves and nuts is passed through the window opening in the jaw portion of the hook holders. The sleeves and nuts on the spinal rod are aligned with the slotted hooks and the threaded portion of the spinal rod is dropped into and through the open slots of the hooks. The sleeves are then slid into the respective cylindrical portion of the slots of the hooks until they seat to secure the hooks to the spinal rod. The nuts are then tightened to, when for example a compression rod is used, apply compression to the spine.

The sleeves will become enclosed by but not pass through the hooks because of the smaller diameter of the bore on the opposite end of the hooks.

The windowed hook holder of the present invention comprises two shank members joined by a hinge means located at a point about one-fifth to one-half, preferably one-fifth to one-third and more preferably about one-fourth the length of the shank portion from one end of the shank. The hinge provides a scissor action between the shank members.

The short end of the shank member is formed into two opposing jaws for firmly grasping small objects. The area immediately behind the jaws is milled or machined out to provide an open area and form a window through the jaw portion of the shank members. The milled out area or window is large enough to allow passage therethrough of a compression rod with sleeves and nuts thereon assembled. The opposite ends of the shank members have joined thereto or formed therewith generally circular openings for fingers to pass through and hold the holder.

Disposed in a position near to and opposite the circular openings between the two shank members is a releasable locking means for locking the scissor action in a fixed position such that an object held in the jaws is firmly held without having to maintain any pressure on the finger openings of the shank members.

A feature of the invention is the use of a hook assembly with a threaded rod to inter-engage the threaded rod with a portion of the spinal column. The hook assembly includes a sleeve or bushing for engaging the threaded rod and surrounding a portion thereof. A base engages the sleeve and has a bore therethrough for receiving the sleeve. A slot is provided in the base on the side or top thereof and is parallel to and communicates with the bore. The slot has a width which is greater than the diameter of the threaded rod and less than the outside diameter of the sleeve so that the threaded rod may pass therethrough and be placed into the slotted base of the hook and held in position by the sleeve which is slipped over the rod and into the bore. A hook or shoe is integrally connected to and projects from the base. A locking system is employed to position the hook assembly with respect to the threaded rod so that the relative position of the hook assembly will remain consistent with respect to the threaded rod. In a preferred embodiment, the locking system is a threaded nut which engages the threaded rod on one side of the sleeve and base. It is contemplated that one of the threaded nuts may be integrally attached to the sleeve to facilitate placement of the sleeve. The bore in the base may be tapered so that the bore engages the sleeve and does not completely pass therethrough. Alternatively, the bore may have a smaller diameter portion which prevents passage of the sleeve completely therethrough. In addition, the base may be provided with opposing openings for engagement of the hook holder.

As discussed above, the slotted hooks are placed on the spinal column and held in position by the windowed hook holders of the present invention. The rod is aligned with the hooks and the sleeves and nuts are spaced along the rod to correspond to the spacing of the positioned hooks. The rod is then passed through the windows in the hook holders, again aligned with the hooks and dropped through the respective slots in the hook bases without disengaging the hook holders from the hooks. The sleeve or bushing is then located within the bore in the base to secure the rod to the hook. The threaded nut is then turned down to achieve compression or distraction, and the entire hook assembly is held in position.

A main feature and advantage of the novel windowed hook holder of the present invention is that it greatly facilitates the installation of the slotted hooks. The surgeon is able to hold each hook and perform the entire procedure without having to disengage the hook holder from the hook. The surgeon can thus maintain control of the hooks at all times and can manipulate and adjust the hooks relative to the compression rod before, during and after insertion of the rod into the slot of each hook.

The slotted hook and windowed hook holder have greatly facilitated compression instrumentation because the rod can be lowered and inserted into the slot of previously positioned hooks without having to disengage the hook holder from the hook.

This system represents a considerable improvement over the Harrington system which requires seating the hooks while attached to the rod or the prior slotted hook system which requires releasing each hook as the rod is seated in the slot of the respective hooks.

Applicant has found that the use of the present method and apparatus has greatly facilitated the installation of the spinal system and has reduced the operating time by about 65% as compared to the Harrington system and about 30% as compared to the prior slotted hook system.

BRIEF DESCRIPTION OF THE DRAWINGS

These features and objects of the invention, as well as others, will become apparent to those skilled in the art by referring to the accompanying drawings in which

FIG. 1 is an illustration of a Harrington distraction rod and a Harrington compression rod engaging the spinal column;

FIG. 2 is a schematic illustration, from the rear, of an individual suffering from scoliotic curvature of the spinal column;

FIG. 3 shows a Cotrel compression rod and a Harrington distraction rod engaging the spinal column and tensioned by a device disclosed in French Pat. No. 2,244,466;

FIG. 4 shows another view of the tensioning device shown in FIG. 3;

FIG. 5 of the drawings is a top plane view of the novel windowed hook holder of the present invention;

FIG. 6 of the drawings is a side view of the FIG. 5 hook holder;

FIG. 7 is a cross-sectional view of the hook assembly of the invention shown in the locked position;

FIG. 8 is a side view of the hook and base portions of the hook assembly;

FIG. 9 is a sectional view of the base of the hook assembly taken along lines 7—7 of FIG. 7;

FIG. 10 is a perspective view showing the hook assembly in position to be engaged;

FIG. 11 of the drawings is a perspective view showing the windowed hook holder engaging a slotted hook and passing a threaded spinal rod through the window opening of the hook holder.

FIG. 12 shows slotted hooks being held in position on a spinal column by a windowed hook holder, alignment of the rod with the hooks and spacing of the sleeves and nuts on a spinal rod;

FIG. 13 shows slotted hooks being held in position by windowed hook holders and passing the spinal rod, sleeves and nuts through the window openings in the hook holders; and FIG. 14 shows slotted hooks being held in place by a windowed hook holder and dropping and insertion of the spinal rod in the slots on the hooks and placing the sleeves in the hooks.

DETAILED DESCRIPTION OF THE INVENTION

The apparatus used to carryout the method of the present invention comprises a windowed hook holder, a slotted hook and smooth cylindrical sleeve, a threaded spinal rod and locking nuts.

The windowed hook holder and its method of use constitute the principle features of the invention. The windowed hook holder allows the operator to hold, manipulate and individually adjust each hook during assembly of the hooks on the spinal rod without at any time during the assembly operation having to release or disengage the hook holders from any of the hooks.

Figure 5:
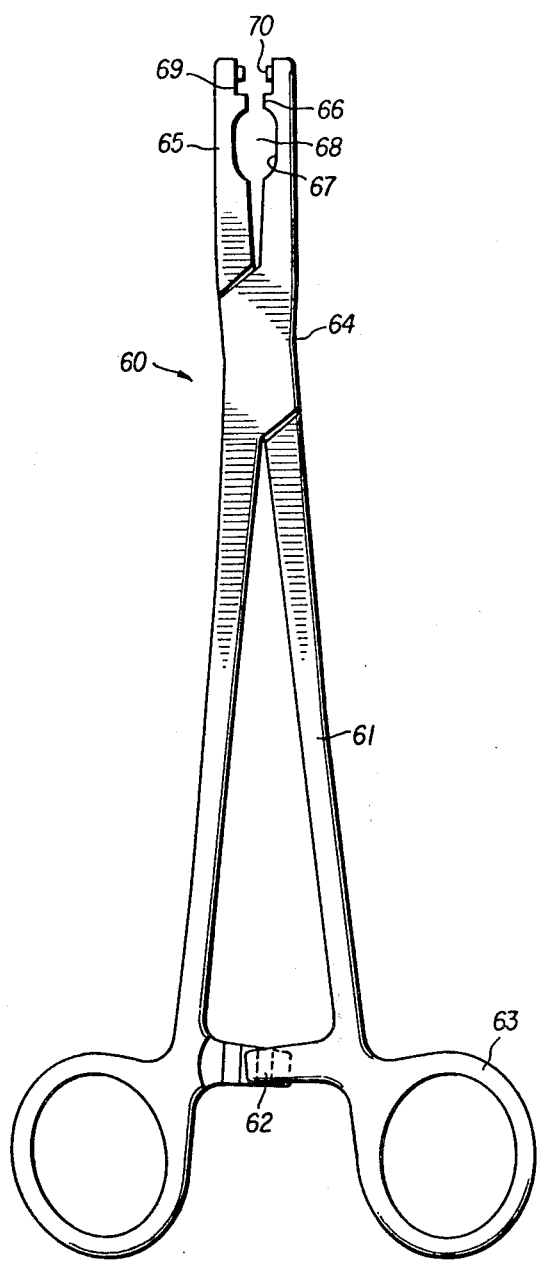
Figure 6:
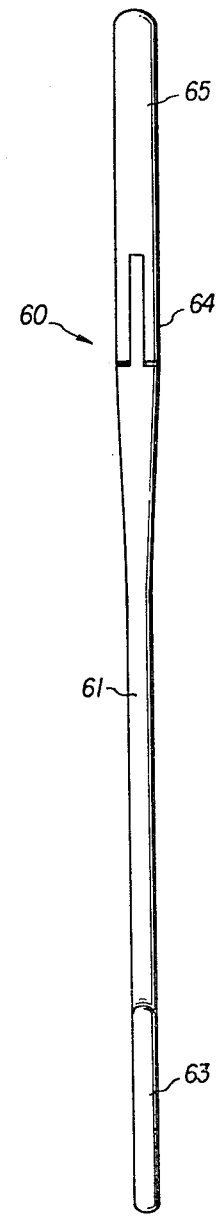
Figure 11:
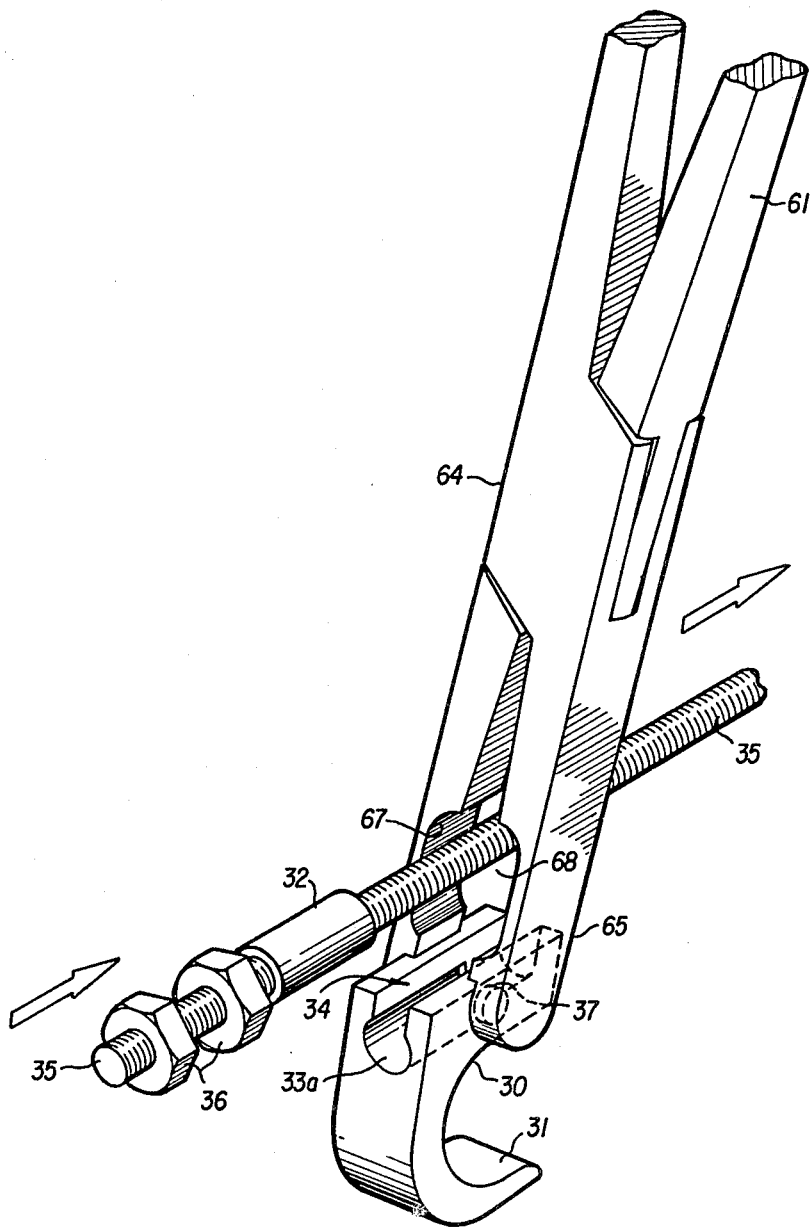

The invention will be more particularly described with reference to FIGS. 5, 6 and 11 of the drawings.

The windowed hook holder 60 of the present invention comprises two shank members 61 joined by a hinge means 64 located at a point about one-fourth the length of the shank member from one end of the shank. The hinge means 64 provides a scissor action between the shank members 61.

The short end of the shank member is formed into two opposing jaws 65 for firmly grasping small objects. The window 68 of the hook holder is formed by machining or milling out an inner part 67 of the jaw portion immediately behind the jaws to form an opening 68. The opening 68 is of sufficient size to allow compression rod 35 with sleeves 32 and nuts 36 assembled on the rod to pass through the opening 68 when the hook holder 60 is in a closed position and/or when the hook holder has a hook 30 firmly held in the jaws 65 of the holder 60. The compression rod 35 with assembled parts can pass through the opening 68 without opening a closed hook holder and/or without disengaging a hook holder 60 from a hook held by the holder.

The jaws 65 of the hook holder 60 can contain two opposing purchasing nubs 70 for engaging mating opening 37 in the sides of the slotted hooks 30. Though it is advantageous to have two purchasing nubs 70, there can be only one nub or none.

The land surfaces 66 may be in contact when the jaws are closed.

The opposite ends of the shank members are joined to or form circular openings 63 for fingers to hold the holder.

Disposed in a position near to and opposite the circular openings between the two shank members is a releasable locking means 62 for locking the scissor action in a fixed position such that an object held in the jaws 65 is firmly held without having to maintain any pressure on the finger openings of the shank members. The locking means 62 illustrated in the drawings consists of two opposing and overlapping stepped bar members which extend inwardly from the shank members towards each other. Other suitable releasable locking means can, however, be used.

Another feature of the invention is the use of the connecting means which forms the hook assembly as illustrated in FIGS. 7 to 10. This hook assembly allows the placement of the hook with engagement of the spinal column before the hook and attached base are connected to the threaded rod. The hook assembly further provides a positive interconnection between the base and hook portions and the threaded rod so that, in the locked position, pivoting or other movement between the threaded rod and base of the hook assembly is not possible.

Figure 1:
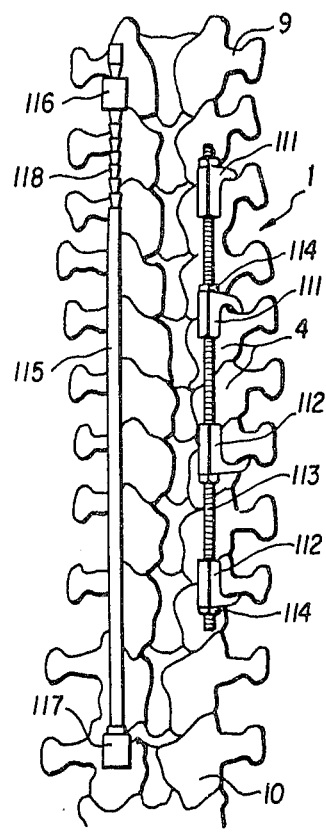
FIGS. 1 to 4 are illustrative of the prior art and FIGS. 5 to 14 are illustrative of the present invention.
Figure 2:
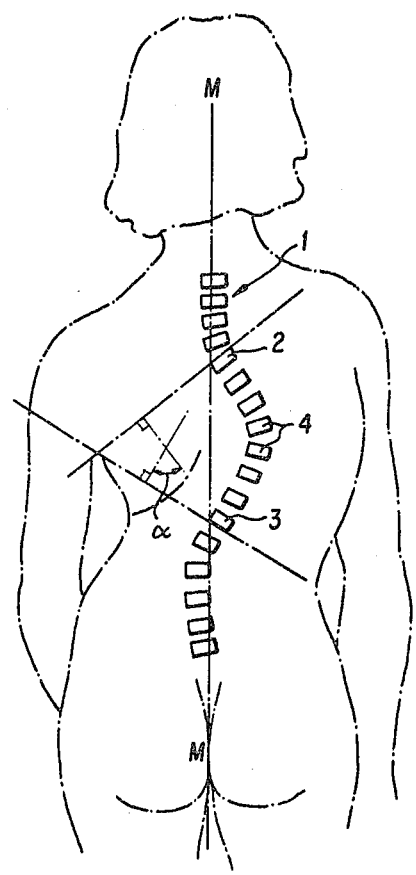
Figure 3:
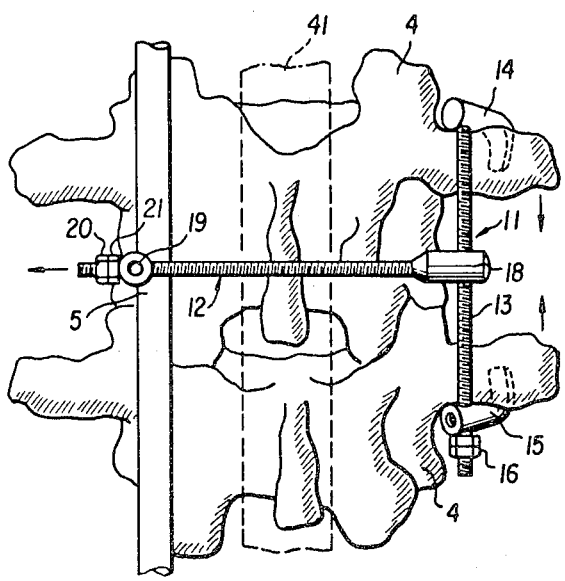
Figure 4:
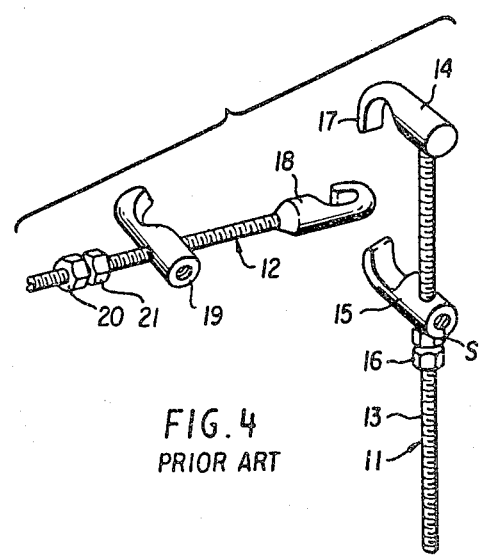
Figure 7:
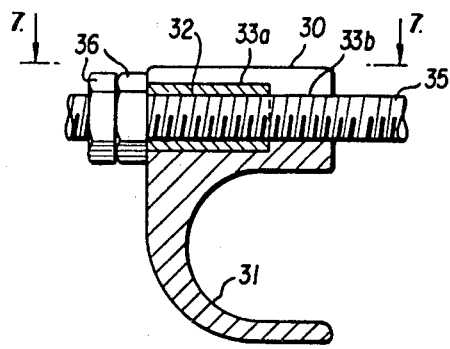
Figure 8:
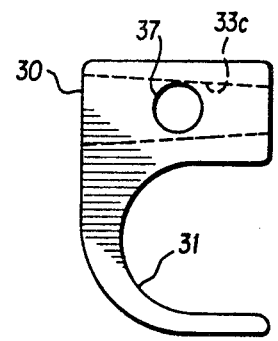

Referring in more detail to the features of FIG. 7, it can be appreciated that threaded rod 35 is somewhat similar to rod 113 shown in FIG. 1. In particular, rod 35 is a threaded rod which interconnects two or more hook means for engaging the spinal column or interengaging a Harrington compression rod and a Harrington distraction rod. It is, therefore, noted that the hook assembly of the invention may be used as a part of a distraction rod, as part of a compression rod or as part of a tensioning means which interconnects a Harrington distraction rod and a Harrington compression rod. In fact, the hook assembly may be used on any surgical system in which engagement of a hook means is require.

The threaded rod 35 carries a sleeve 32 which surrounds the rod and slides along the rod for free positioning. The base portion 30 of the hook assembly is integrally connected to a hook portion 31 which particularly engages the spinal column or rod which is to be the anchoring means. Bore 33a is longitudinally located within the base portion 30 and is sized to accept the sleeve 32. Bore 33b is provided and has a diameter which is less than the outside diameter of the sleeve 32 so that the sleeve is prevented from completely passing through bore 33a and through the base portion 30 of the hook assembly. Alternatively, as shown in FIG. 6, the bore within the base portion 30 may be tapered bore 33c which performs the same function as bores 33a and 33b.

Figure 9:
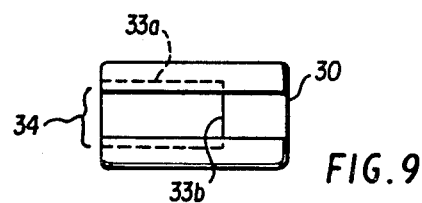
Figure 10:
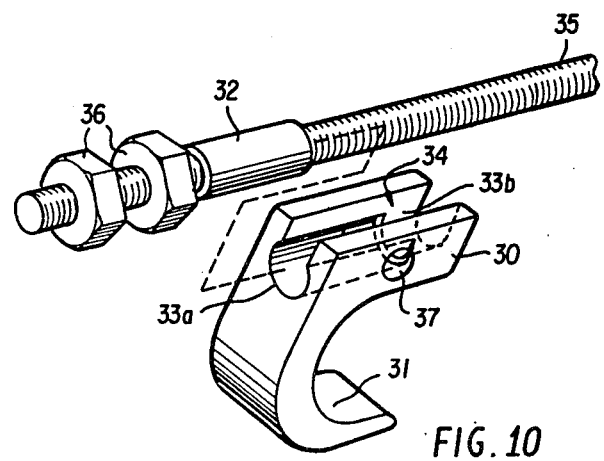

A slot 34, as best shown in FIGS. 9 and 10, is parallel to the bore 33a and in communication with the bore 33a to form an opening in the base 30. The size of the slot 34 in relation to the sleeve 32 and threaded rod 35 forms an important feature of the hook. In the preferred embodiment, the slot 34 forms an opening within the base 30 so that the width of slot 34 is greater than the diameter of rod 35 but less than the outside diameter of sleeve 32. The result of this dimension is that the slot 34 allows the rod 35 to be slipped into the hook assembly and then the sleeve 31 is moved along the rod 35 to engage the hook assembly. This movement can be appreciated by referring to the dotted lines in FIGS. 9 and 10. Once the base 30 is in position around the sleeve 32 so that the sleeve 32 is located within bore 33a and abuts the shoulder between bore 33a and 33b, locking nuts 36 may be turned to lock the position of sleeve 32, base portion 30 and integrally connected hook portion 31 into position with respect to the threaded rod 35.

In an alternative embodiment, it is contemplated that the sleeve 32 may be integrally connected to a locking nut 36 so that the particular position of the sleeve 32 is determined by the position of the locking nut to which it is connected. In some operations, this type of structure allows for the manipulation of the hook assembly in a more efficient fashion.

The base portion 30 of the hook assembly may be provided with engaging openings 37. The openings, which are opposing, are provided so that the entire base portion 30 and integrally connected hook portion 31 may be more easily handled by the hook holder of the present invention. These engaging openings are especially necessary when the apparatus being implanted is of an extremely small nature and manipulation of the base portion 30 and integrally connected hook portion 31 becomes difficult with human fingers. It is also contemplated that other engaging means, not shown, may be provided on the base portion 31, such as notches, multiple openings, transverse bores, projections or protrusions with corresponding mating members on the hook holder jaws.

It is, therefore, apparent that the hook assembly allows for the engagement of the hook portion 31 by manipulation of the base portion 30 before the base portion is slideably engaged by the sleeve 32 carried by the threaded rod 35. With the hook portion 31 engaged to an anchor, such as the spinal column, the threaded rod 35 may be slipped through the slot 34 and the sleeve 32 is then moved along the threaded rod 34 into the bore 33a. With the threaded rod 35 and sleeve 32 in place, the entire hook assembly is retained on the rod 35 by locking nuts 36 and compression or distraction may be achieved by advancing a locking nut in the proper direction. This allows the surgeon to place each hook on the spine, tilting or manipulating the hook as required to achieve a good purchase. This often avoids the partial laminectomy that is sometimes necessary with the Harrington systems of the prior art.

A preferred embodiment of the method of the present invention is described with reference to FIGS. 12 to 14 of the drawings.

The spine 9, 10 shown in dotted lines is prepared in the regular manner. The purchase sites for the hooks are cut around the transverse processes or lamina using a sharp slotted hook. The blunt slotted hooks 30 are then placed at each vertebral level and controlled by the surgeon and assistants by holding them firmly with the windowed hook holders 60 of the present invention.

Figure 12:
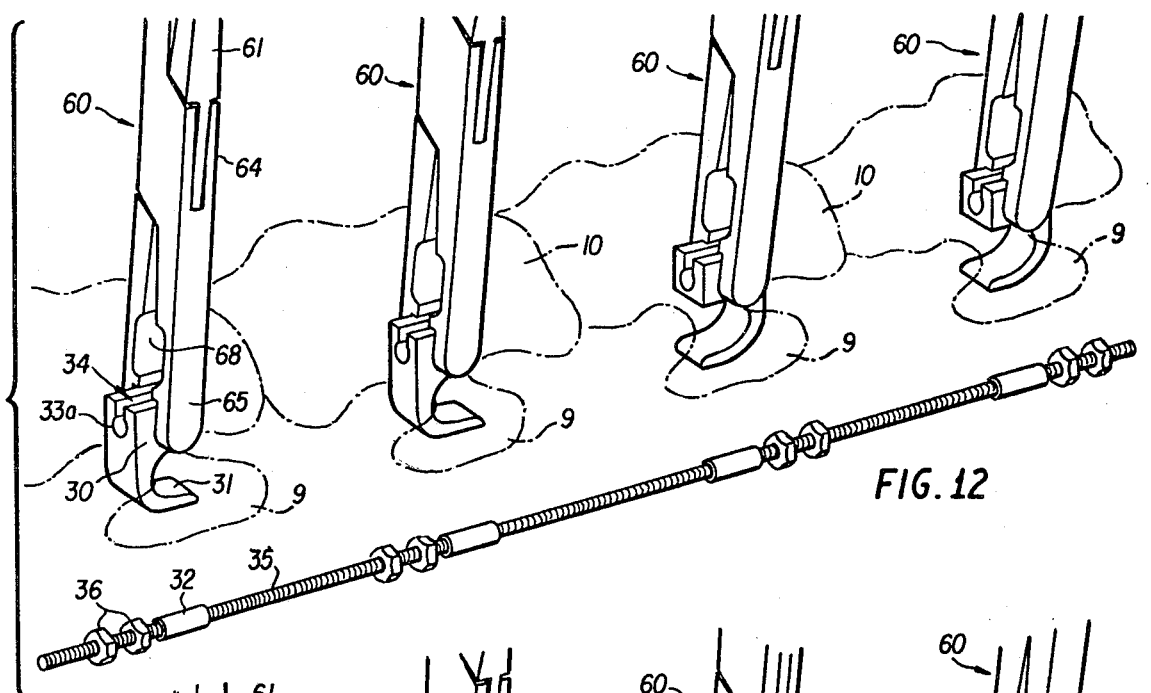

The sleeves 32 and nuts 36 are then spaced along the compression rod 35 to align them approximately with the corresponding hooks 30 on the spinal column 9, 10 to which they are to be attached (FIG. 12).

Figure 13:
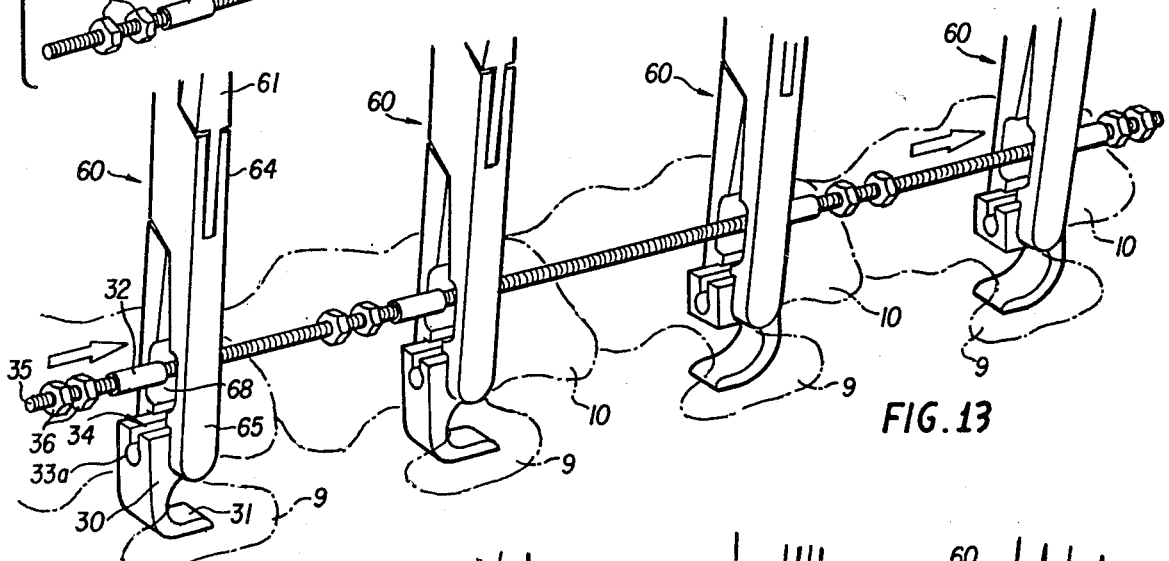
Figure 14:
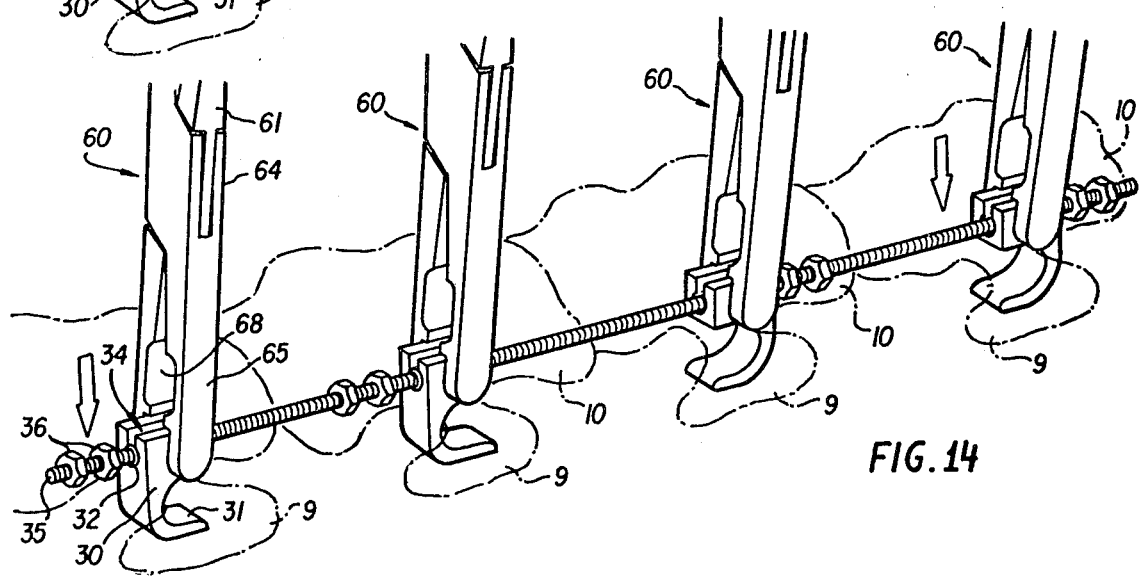

The compression rod 35 with the spaced sleeves 32 and nuts 36 is then passed through the window 68 openings in the hook holder 60 (FIG. 13). While controlling the slotted hooks 30 with the windowed holders 60, the compression rod 35 is pressed downwardly into the slots 33b of the hooks 30 (FIG. 14).

The sleeves 32 are then moved forwardly into the slot hook from behind to secure the hook to the rod (FIG. 7). The engaging of the sleeve 32 with the slot 33b firmly holds the rod 35 within the hook 30 (FIG. 14).

Compression is accomplished as before by advancing the first or closest of the nuts 36 against the sleeve 32 and hook 30 and the first nut 36 then locked in place by the second nut 36.

The use of the slotted hook and windowed hook holder has greatly facilitated spinal system installation because the slotted hooks can be individually held in place with the windowed hook holder, adjusted as necessary, and the spinal rod passed through the opening in the windowed hook holder, aligned with the hooks and dropped into place through the slotted hooks without having at any time to release the hooks or disengage the hook holder from the hooks.

The method and apparatus of the present invention can be used for the instrumentation of (1) kyphotic deformities, (2) the convex side of a thoracic scoliosis, and (3) unstable spine fractures and fracture dislocations. They can also be helpful in providing the extra stability required in the management of neuromuscular scoliosis.

The combination of distraction and compression instrumentation with transverse compression links provides greater stability than can be achieved by utilizing either system alone.

The use of the method and apparatus described above has shown that a substantial reduction in surgical time, as compared to the Harrington system and prior slotted hook system, can be achieved.

Any slotted hook style may be adapted to this design or the sleeve or bushing employed can have a square, hexagonal or other shape. However, the internal shape of the sleeve must be complementary and corresponding to the external shape of the threaded rod and the external shape of the sleeve must be equivalent to or complementary with the internal shape of the bore and the base.

Furthermore, although the present invention has been disclosed and discussed with particular regard to its exceptional advantages in terms of devices for the treatment of spinal fracture and scoliosis, it may be understood that the invention may be employed in several surgical as well as industrial applications wherein a rod engages a portion by means of a hook which requires manipulation about the portion. In addition, although the preferred embodiment contemplates a metallic structure, the invention may be comprised of any suitable form-retaining material.

Various changes may be made to the details of the invention, as disclosed, without sacrificing the advantages thereof or departing from the scope of the appended claims.

What is claimed is:

1. A method for installing a hook and rod assembly which comprises grasping slotted hooks with hook holders each said hook holder having jaws and a windowed opening immediately behind the jaws, said windowed opening being sufficiently large such as to allow passage therethrough of a rod and spaced locking means when said hook holders are holding said hooks in alignment on a spinal column, said jaws firmly holding said hooks, placing the hooks at desired positions and holding each hook in place with said hook holders, placing locking means on the rod for locking the hooks to the rod and spacing the locking means to align them approximately with corresponding hooks to which they are to be attached, passing the rod with the spaced locking means through the windowed opening in each of the hook holders, while controlling and maintaining the position of the slotted hooks with the respective hook holders, aligning the locking means with the respective slotted hooks, pressing said rod into the slots of said hooks, connecting the locking means to the hooks to secure the rod to the hooks and to firmly hold the rod within the hooks.

2. The process of claim 1 wherein said locking means comprises first and second nuts and the first nut is advanced against the hook, and the second nut is advanced to lock the first nut in place against the hook.

3. The process of claim 1 wherein said hooks are held in position with said hook holders and their position adjusted by said hook holders as the rod is passed through the windowed openings, aligning the locking means with said hooks without releasing said hooks or disengaging the hook holders from the hooks, and pressing said rod into the slots of said hooks.

4. A method for installing a hook and rod assembly on a spinal column which comprises grasping slotted hooks having a bore in communication with a parallel slot, with hook holders, each said hook holder having jaws and a windowed opening immediately behind the jaws, said windowed opening being sufficiently large so as to allow passage therethrough of a rod and spaced locking means when said hook holders are holding said hooks in alignment on said spinal column, each said locking means comprising sleeve means and nuts, said jaws firmly holding said hooks, placing the hooks at each vertebral level and holding each hook in place with one of said windowed hook holders, placing said locking means on the rod and spacing said locking means to align them approximately with corresponding hooks on the spinal column, passing the rod with the spaced locking means through the windowed openings in the hook holders, while controlling and maintaining the position of the slotted hooks with the respective hook holders, aligning each locking means comprising sleeve means and nuts with a respective slotted hook, pressing said rod into the slots of said hooks, moving the sleeve means forwardly into the bores of the respective slots to secure the rod to the hooks and to firmly hold the rod within the hooks and moving the nuts forwardly to lock the hooks in place on the rod.

5. The process of claim 4 wherein there are two nuts associated with each sleeve means and the first of the nuts is advanced against the sleeve means and hook, and the second of the nuts is advanced to lock the first nut in place against the hook and sleeve means.

6. The process of claim 4 wherein said hooks are held in position with said hook holders and their positions adjusted by said hook holders as said rod is passed through the windowed openings, aligning the sleeve means and nuts with said hooks without releasing said hooks or disengaging the hook holders from the hooks, and pressing said rod into the slots of said hooks.

7. A method for installing a hook and rod assembly which comprises grasping slotted hooks with hook holders, each said hook holder having jaws and a windowed opening immediately behind the jaws, each said windowed opening being sufficiently large such as to allow passage therethrough of a rod and spaced locking means when said hook holders are holding said hooks in alignment on a spinal column, said jaws firmly holding said hooks, placing the hooks at desired positions and holding each hook in place with a respective hook holder, placing said locking means on the rod for locking the hooks to the rod and spacing the locking means to align them approximately with corresponding hooks to which they are to be attached, passing the rod with the spaced locking means through the windowed openings in the hook holders, while controlling and maintaining the position of the slotted hooks with the respective hook holders, aligning the locking means with their respective slotted hooks and pressing said rod into the slots of said hooks without releasing said hooks or disengaging the hook holders from the hooks, and connecting the locking means to the hooks to secure the rod to the hooks and to firmly hold the rod within the hooks.

8. A method for installing a hook and rod assembly on a spinal column which comprises grasping slotted hooks having a bore in communication with a parallel slot, with hook holders, each said hook holder having jaws and a windowed opening immediately behind the jaws, each said windowed opening being sufficiently large such as to allow passage therethrough of a rod and spaced locking means when said hook holders are holding said hooks in alignment on said spinal column, each said locking means comprising sleeve means and nuts, said jaws firmly holding said hooks, placing the hooks at each vertebral level and holding each hook in place with a respective hook holder, placing said locking means on the rod and spacing said locking means to align them approximately with corresponding hooks on the spinal column, passing the rod with said spaced locking means through the windowed openings in the hook holders, while controlling and maintaining the position of the slotted hooks with their respective hook holders, aligning each locking means with a respective slotted hook and pressing said rod into the slots of said hooks without releasing said hooks or disengaging the hook holders from the hooks, and moving the sleeve means of the locking means forwardly into the bores of the respective slots to secure the rod to the hooks and to firmly hold the rod within the hooks and moving the nuts forwardly to lock the hooks in place on the rod.

* * * * *